US012782351B2

(12) United States Patent
Aburaya et al.

(10) Patent No.: US 12,782,351 B2
(45) **Date of Patent: *Nov. 3, 2026**

(54) IMMUNOCHROMATOGRAPHY

(71) Applicant: FUJIFILM Corporation, Tokyo (JP)

(72) Inventors: Yoshihiro Aburaya, Ashigarakami-gun (JP); Junichi Katada, Ashigarakami-gun (JP); Atsuhiko Wada, Ashigarakami-gun (JP); Dai Ujihara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1093 days.

This patent is subject to a terminal disclaimer.

(21) Appl. No.: 17/852,053

(22) Filed: Jun. 28, 2022

(65) Prior Publication Data

US 2022/0334111 A1 Oct. 20, 2022

Related U.S. Application Data

(63) Continuation of application No. PCT/JP2020/042912, filed on Nov. 18, 2020.

(30) Foreign Application Priority Data

Jan. 31, 2020 (JP) ................................ 2020-014657

(51) Int. Cl.

*G01N 33/543* (2006.01)
*G01N 33/532* (2006.01)
*G01N 33/553* (2006.01)

(52) U.S. Cl.

CPC ..... *G01N 33/54393* (2013.01); *G01N 33/532* (2013.01); *G01N 33/553* (2013.01)

(58) Field of Classification Search

CPC ........... G01N 33/54393; G01N 33/532; G01N 33/553; G01N 2469/10; G01N 33/5695; G01N 33/54388

See application file for complete search history.

(56) References Cited

U.S. PATENT DOCUMENTS

2011/0287446 A1 11/2011 Kanda et al.
2014/0087367 A1 3/2014 Wada
2014/0154713 A1 6/2014 Mizuno et al.

FOREIGN PATENT DOCUMENTS

JP 5728453 B2 6/2015
WO WO 2010/092958 A1 8/2010
WO WO 2012/173002 A1 12/2012
WO WO 2019/186486 A1 10/2019

OTHER PUBLICATIONS

Harpole et al. Current state of the art for enhancing urine biomarker discovery. Expert Rev Proteomics. Jun. 2016 ; 13(6): 609-626. (Year: 2016).*

Thermo Scientific, Tech Tip # 4. Batch and spin cup methods for affinity purification of proteins.2008, pp. 1-3; 2008 Thermo Fisher Scientific Inc. Pierce Biotechnology, Rockford, IL 61105 USA. (Year: 2008).*

Paris et al. Urine lipoarabinomannan glycan in HIV-negative patients with pulmonary tuberculosis correlates with disease severity. Sci. Transl. Med. 2017, vol. 9, No. 420, pp. 1-11. (Year: 2017).*

Du et al. Chromatographic analysis of the acidic and basic species of recombinant monoclonal antibodies. mAbs vol. 4, Issue 5, pp. 578-585; Sep./Oct. 2012 (Year: 2012).*

International Preliminary Report on Patentability and English translation of the Written Opinion of the International Searching Authority (Forms PCT/IB/326, PCT/IB/373 and PCT/ISA/237) for International Application No. PCT/JP2020/042912, dated Aug. 11, 2022.

International Search Report (Form PCT/ISA/210) for International Application No. PCT/JP2020/042912, dated Feb. 9, 2021, with English translation.

Broger et al., "Novel lipoarabinomannan point-of-care tuberculosis test for people with HIV: a diagnostic accuracy study," Lancet Infect Dis, vol. 19, Aug. 2019 (Published online May 30, 2019), pp. 852-861.

(Continued)

*Primary Examiner* — Shafiqul Haq
(74) *Attorney, Agent, or Firm* — Birch, Stewart, Kolasch & Birch, LLP

(57) ABSTRACT

An immunochromatography includes steps of mixing a specimen capable of containing an antigen and a modified particle, which is a particle modified with a substance having a specific affinity to the antigen, to obtain a mixture containing particle composite bodies; sedimenting the particle composite bodies in the mixture using a centrifuge; dissociating the sedimented particle composite bodies into the particles and the antigen by mixing the sedimented particle composite bodies with a dissociation solution, recovering an antigen-concentrated solution by sedimenting the dissociated particles using a centrifuge; neutralizing the antigen-concentrated solution using a neutralization solution; spreading particle composite bodies for labeling on an insoluble carrier having a reaction site, in a state where the particle composite bodies for labeling, which are composite bodies of the antigen in the neutralized antigen-concentrated solution and a modified particle for labeling, are formed; and capturing the particle composite bodies for labeling at the reaction site.

6 Claims, 1 Drawing Sheet

(56) References Cited

OTHER PUBLICATIONS

Extended European Search Report for corresponding European Application No. 20916500.0, dated Jan. 17, 2023.
Fredolini et al., "Immunocapture strategies in translational proteomics," Expert Rev. Proteomics, vol. 13, No. 1, 2016, pp. 83-98.
Moreau, "Urine LAM detection: what is the future?", Advanced TB Diagnostics, Jun. 19, 2018, pp. 1-32.
Savolainen et al , "Modification of Clearview Tuberculosis (TB) Enzyme-Linked Immunosorbent Assay for TB Patients Not Infected with HIV," Clinical and Vaccine Immunology, vol. 20, No. 9, Sep. 2013, pp. 1479-1482.
Zherdev et al., "Ways to Reach Lower Detection Limits of Lateral Flow Immunoassays," Rapid Test—Advances in Design, Format and Diagnostic Applications, InTechOpen, Sep. 26, 2018, pp. 10-43 (37 pages total).

* cited by examiner

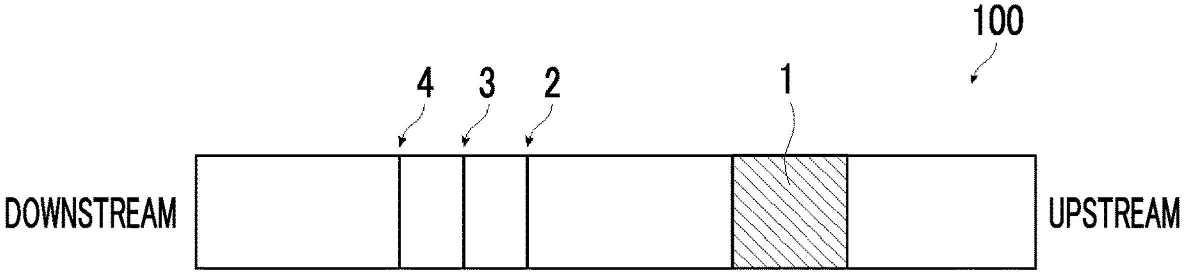
100
4
3
2
1
DOWNSTREAM
UPSTREAM

IMMUNOCHROMATOGRAPHY

CROSS-REFERENCE TO RELATED APPLICATIONS

This application is a Continuation of PCT International Application No. PCT/JP2020/042912 filed on Nov. 18, 2020, which claims priority under 35 U.S.C § 119(a) to Japanese Patent Application No. 2020-014657 filed on Jan. 31, 2020. Each of the above application(s) is hereby expressly incorporated by reference, in its entirety, into the present application.

BACKGROUND OF THE INVENTION

1. Field of the Invention

The present invention relates to immunochromatography.

2. Description of the Related Art

Immunochromatography is frequently used these days since the operation is easy and measurement can be carried out in a short time.

For example, in a case where an antigen such as influenza virus or lipoarabinomannan (LAM) is detected by immunochromatography, the following operations are carried out.

First, in a case where a substance that serves as a label modified with an antibody, for example, a gold particle is used, a modified gold particle is prepared and mixed with a specimen containing an antigen. The modified gold particle binds to the antigen to form composite bodies. In this state, in a case where these composite bodies are spread on an insoluble carrier having a detection line (a test line) onto which an antibody that specifically reacts with an antigen is applied, the composite bodies react with the antibody on the detection line and are captured, and detection is confirmed visually or in other manners.

Examples of such immunochromatography include the method disclosed in JP5728453B.

SUMMARY OF THE INVENTION

These days, an immunodiagnostic method applicable to a specimen having an extremely low antigen concentration is desired, and regarding immunochromatography, there is also a demand for a method having higher sensitivity than the method in the related art (for example, the method disclosed in JP5728453B).

In consideration of the above circumstances, an object of the present invention is to provide immunochromatography having high detection sensitivity.

As a result of diligent studies on the above-described objects, inventors of the present invention have found that the above-described objects can be achieved by concentrating a specimen by a predetermined method and have reached the present invention.

That is, the inventors of the present invention have found that the object can be achieved by the following configurations.

(1) Immunochromatography comprising:

- a mixing step of mixing a specimen capable of containing an antigen and a modified particle, which is a particle modified with a substance having a specific affinity to the antigen, to obtain a mixture containing particle composite bodies which are composite bodies of the antigen and the modified particle;
- a sedimentation step of sedimenting the particle composite bodies in the mixture using a centrifuge;
- a dissociation step of mixing the sedimented particle composite bodies with a dissociation solution that is an alkaline or acidic solution, where an amount of the dissociation solution is smaller than an amount of the specimen capable of containing an antigen, to dissociate the particle composite bodies into the particles and the antigen;
- a recovery step of sedimenting the dissociated particles using a centrifuge to recover an antigen-concentrated solution;
- a neutralization step of neutralizing the antigen-concentrated solution using a neutralization solution to obtain a neutralized antigen-concentrated solution;
- a spreading step of spreading particle composite bodies for labeling on an insoluble carrier having a reaction site at which a second binding substance capable of binding to the antigen has been immobilized, in a state where the particle composite bodies for labeling which are composite bodies of the antigen in the neutralized antigen-concentrated solution and a modified particle for labeling which is a particle for labeling modified with a first binding substance capable of binding to the antigen are formed; and
- a capturing step of capturing the particle composite bodies for labeling at the reaction site of the insoluble carrier.

(2) The immunochromatography according to (1), in which the spreading step is a step of spreading gold particle composite bodies for labeling on the insoluble carrier having the reaction site at which the second binding substance capable of binding to the antigen has been immobilized, in a state where the gold particle composite bodies for labeling which are composite bodies of the antigen in the neutralized antigen-concentrated solution and a modified gold particle which is a gold particle modified with the first binding substance capable of binding to the antigen are formed,

- the capturing step is a step of capturing the particle composite bodies for labeling, at the reaction site of the insoluble carrier, and
- the immunochromatography further includes a silver amplification step of silver-amplifying the particle composite bodies for labeling captured in the capturing step.

(3) The immunochromatography according to (1) or (2), in which the modified particle that is used in the mixing step has a particle diameter of 50 nm to 3,000 nm.

(4) The immunochromatography according to any one of (1) to (3), in which a ratio of the dissociation solution to the specimen capable of containing an antigen is 1/5 or less in terms of mass ratio.

(5) The immunochromatography according to any one of (1) to (4), in which the specimen capable of containing an antigen is urine.

(6) The immunochromatography according to any one of (1) to (5), in which the antigen is a sugar chain.

(7) The immunochromatography according to any one of (1) to (6), in which the dissociation solution contains NaOH or HCl.

(8) The immunochromatography according to any one of (1) to (7), in which the neutralization solution contains HCl and at least one selected from the group consisting of tricine, Tris, HEPES, acetamidoglycine, glycinamide, and vicine, or contains NaOH and at least one selected from the group consisting of tricine, Tris, HEPES, acetamidoglycine, glycinamide, and vicine.

(9) The immunochromatography according to any one of (1) to (8), in which the antigen is lipoarabinomannan.

As described below, according to the present invention, it is possible to provide immunochromatography having high detection sensitivity.

BRIEF DESCRIPTION OF THE DRAWINGS

FIG. 1 is a schematic view illustrating an aspect of an insoluble carrier that is used in a method according to the embodiment of the present invention.

DESCRIPTION OF THE PREFERRED EMBODIMENTS

Immunochromatography according to the embodiment according to the embodiment of the present invention will be described below.

In the present specification, the numerical value range indicated by using "to" means a range including the numerical values before and after "to" as the lower limit value and the upper limit value, respectively.

In addition, in the present specification, one kind of each component may be used alone, or two or more kinds thereof may be used in combination. In a case where two or more kinds of each component are used in combination, the content of the component indicates a total content unless otherwise specified.

Further, in the present specification, "the detection sensitivity and the signal/noise ratio (the S/N ratio) are further improved" is also described as "the effects and the like of the present invention are more excellent".

Further, in the present specification, the process from the mixing step to the neutralization step is also referred to as a "concentration step", and the process after the spreading step is also referred to as a "detection step".

The immunochromatography according to the embodiment of the present invention (hereinafter, also referred to as "the method according to the embodiment of the present invention") is immunochromatography including;

- a mixing step of mixing a specimen capable of containing an antigen and a modified particle, which is a particle modified with a substance having a specific affinity to the antigen, to obtain a mixture containing particle composite bodies which are composite bodies of the antigen and the modified particle,
- a sedimentation step of sedimenting the particle composite bodies in the mixture using a centrifuge,
- a dissociation step of mixing the sedimented particle composite bodies with a dissociation solution that is an alkaline or acidic solution, where an amount of the dissociation solution is smaller than an amount of the specimen capable of containing an antigen, to dissociate the particle composite bodies into the particles and the antigen;
- a recovery step of sedimenting the dissociated particles using a centrifuge to recover an antigen-concentrated solution;
- a neutralization step of neutralizing the antigen-concentrated solution using a neutralization solution to obtain a neutralized antigen-concentrated solution,
- a spreading step of spreading particle composite bodies for labeling on an insoluble carrier having a reaction site at which a second binding substance capable of binding to the antigen has been immobilized, in a state where the particle composite bodies for labeling which are composite bodies of the antigen in the neutralized antigen-concentrated solution and a modified particle for labeling which is a particle for labeling modified with a first binding substance capable of binding to the antigen are formed, and
- a capturing step of capturing the particle composite bodies for labeling at the reaction site of the insoluble carrier.

It is presumed that since the method according to the embodiment of the present invention has such a configuration, the above effects can be obtained. The reason for this is not clear; however, it is conceived to be as follows.

In general, a specimen contains impurities such as low molecular weight components and salts, in addition to water. For example, in a case where the specimen is urine, it contains impurities such as urea. From the studies by inventors of the present invention, it was found that in a case where the water in the specimen is simply volatilized, these impurities are concentrated together with an antigen, and the antigen-antibody reaction is inhibited, whereby the detection sensitivity is decreased. That is, it is known that the effect of improving the detection sensitivity by concentration cannot be sufficiently obtained.

The method according to the embodiment of the present invention is based on the above findings. That is, in the method according to the embodiment of the present invention, a specimen capable of containing an antigen is concentrated by a predetermined method, and thus the antigen is selectively concentrated, and the above-described decrease in detection sensitivity hardly occurs. As a result, it is conceived that extremely high detection sensitivity is achieved.

Hereinafter, each of the steps included in the method according to the embodiment of the present invention will be described.

[Mixing Step]

The mixing step is a step of mixing a specimen capable of containing an antigen and a modified particle, which is a particle modified with a substance having a specific affinity to the antigen, to obtain a mixture containing particle composite bodies which are composite bodies of the antigen and the modified particle.

[Specimen]

The specimen that is used in the mixing step is not particularly limited as long as it is a specimen capable of containing an antigen. Examples of such a specimen include a biological specimen, particularly a biological specimen of animal origin (particularly, of human origin) such as a body fluid (for example, blood, serum, plasma, spinal fluid, tear fluid, sweat, urine, pus, nasal mucus, or sputum) or excrement (for example, feces), an organ, a tissue, a mucous membrane or skin, a scraped test sample (a swab) that is conceived to contain these substances, mouthwash fluid, and an animal and a plant themselves or a dried substance thereof.

The specimen is preferably a solution and more preferably urine due to the reason that the effects and the like of the present invention are more excellent.

<Antigen>

Examples of the antigen include a fungus, a bacterium (for example, the tubercle bacillus or lipoarabinomannan (LAM) included in the tubercle bacillus), a virus (for example, an influenza virus), and a nuclear protein thereof. It is noted that LAM is a major antigen in tuberculosis, and it is a glycolipid which is a major constitutional component of the cell membrane and the cell wall.

The antigen is preferably an antigen which is a sugar chain (particularly a glycolipid) and more preferably LAM due to the reason that the effects and the like of the present invention are more excellent.

<Pretreatment of Specimen>

Regarding the above specimen, it is possible to use the specimen as it is or in a form of an extraction solution obtained by extracting the antigen using an appropriate solvent for extraction, in a form of a diluent solution obtained by diluting an extraction solution with an appropriate diluent, or in a form in which an extraction solution has been concentrated by an appropriate method.

As the solvent for extraction, it is possible to use a solvent (for example, water, physiological saline, and a buffer solution) that is used in a general immunological analysis method, or a water-miscible organic solvent with which a direct antigen-antibody reaction can be carried out by being diluted with such a solvent.

[Modified Particle]

The modified particle that is used in the mixing step is a particle modified with a substance having a specific affinity to the antigen.

<Particle>

The particle is not particularly limited. Specific examples of the particle include a metal particle, a ceramic particle, and a polymer particle. Among them, a metal particle or a polymer particle is preferable due to the reason that the effects and the like of the present invention are more excellent.

The metal of the metal particle is not particularly limited; however, specific examples thereof include copper, chromium, lead, nickel, gold, silver, platinum, tin, zinc, and iron. Among them, it is preferably iridium, platinum, or gold, which is the precious metal, and it is more preferably gold, due to the reason that the effects and the like of the present invention are more excellent.

The polymer of the polymer particles is not particularly limited; however, specific examples thereof include polyurethane, polystyrene, poly(meth)acrylate, and a diene-based polymer. Among them, it is preferably polystyrene due to the reason that the effects and the like of the present invention are more excellent.

(Particle Diameter)

The particle diameter of the particle and the particle diameter of the modified particle are not particularly limited; however, they are preferably 1 nm to 10 more preferably 10 nm to 5 and still more preferably 50 nm to 3 due to the reason that the effects and the like of the present invention are more excellent.

It is noted that in the present specification, the particle diameter can be measured with a commercially available particle diameter distribution meter or the like. As a method of measuring the particle size distribution, optical microscopy, confocal laser microscopy, electron microscopy, atomic force microscopy, static light scattering method, laser diffraction method, dynamic light scattering method, centrifugal sedimentation method, electric pulse measurement method, chromatography method, ultrasonic attenuation method, and the like are known, and apparatuses corresponding to the respective principles are commercially available. As the method of measuring a particle diameter, a dynamic light scattering method can be preferably used due to the particle diameter range and the ease of measurement. Examples of the commercially available measuring device using dynamic light scattering include NANOTRAC UPA (Nikkiso Co., Ltd.), a dynamic light scattering type particle size distribution measuring device LB-550 (HORIBA, Ltd.), and a Fiber-Optics Particle Size Analyzer FPAR-1000 (Otsuka Electronics Co., Ltd.). In the present invention, the average particle size is obtained as a value of a median diameter (d=50) measured at a measurement temperature of 25° C.

(Specific Gravity)

The specific gravity of the particle is preferably more than 1, more preferably 2 or more, and still more preferably 3 or more, due to the reason that the effects and the like of the present invention are more excellent. The upper limit of the specific gravity of the particle is not particularly limited, however, it is preferably 30 or less due to the reason that the effects and the like of the present invention are more excellent. In a case where the particle is a metal particle, it is preferably a metal having a high specific gravity.

It is preferable to use the above-described precious metal having a specific gravity of about 20.

<Substance Having a Specific Affinity to Antigen>

The substance having a specific affinity to the antigen is not particularly limited; however, due to the reason that the effects and the like of the present invention are more excellent, it is preferably a protein, more preferably an antibody (for example, a polyclonal antibody or a monoclonal antibody), and from the viewpoint of achieving higher detection sensitivity, it is still more preferably a monoclonal antibody.

The above antibody is not particularly limited. However, it is possible to use, for example, an antiserum prepared from a serum of an animal immunized with an antigen, or an immunoglobulin fraction purified from an antiserum. In addition, it is possible to use a monoclonal antibody obtained by cell fusion using spleen cells of an animal immunized with an antigen, or a fragment thereof [for example, $F(ab')_2$, Fab, Fab', or Fv]. The preparation of these antibodies can be carried out by a conventional method.

In a case where the antigen is LAM, examples of the substance having a specific affinity to an antigen include the A194-01 antibody described in WO2017/139153A. The entire content disclosed in WO2017/139153A relating to the A194-01 antibody is incorporated in the present specification as a part of the disclosure of the present specification.

In a case where the antigen is LAM, other examples of the substance having a specific affinity to an antigen include the antibody having a sequence described as MoAb1 in paragraph No. [0080] of WO2013/129634A.

The entire content disclosed in WO2013/129634A relating to the MoAb1 antibody is incorporated in the present specification as a part of the disclosure of the present specification.

<Method of Manufacturing Modified Particle>

The method of manufacturing the modified particle is not particularly limited, and a known method can be used.

In a case where the particle is a gold particle, examples thereof include a chemical bonding method such as a method of utilizing the fact that gold and an SH group are chemically bonded and carrying out immobilization with an Au—S bond that is generated on the Au surface when an SH bond of an antibody is cleaved in a case where the SH bond thereof approaches the gold particle.

Further, examples thereof include a method of activating a particle having a —COOH terminal with 1-ethyl-3-(3-dimethylaminopropyl)carbodiimide (EDC) to carry the antibody on the particle.

[Mixing]

In the mixing step, the specimen and the modified particle are mixed.

As a result, in a case where the specimen contains an antigen, the antigen in the specimen reacts with a substance having a specific affinity to the antigen of the modified particle, whereby particle composite bodies which are composite bodies of the antigen and the modified particle are formed in the specimen. On the other hand, in a case where the specimen does not contain an antigen, the particle composite bodies are not formed.

[Sedimentation Step]

The sedimentation step is a step of sedimenting the particle composite bodies in the mixture obtained in the above-described mixing step, by using a centrifuge.

The centrifugal separation condition of the centrifuge is not particularly limited. However, the centrifugal force is preferably 100 to 1,000,000 G and more preferably 1,000 to 10,000 G, and the time is preferably 1 to 1,000 minutes and more preferably 1 to 100 minutes, due to the reason that the effects and the like of the present invention are more excellent.

[Dissociation Step]

The dissociation step is a step of mixing the sedimented particle composite bodies obtained by removing the supernatant solution generated in the above-described sedimentation step with a dissociation solution that is an alkaline or acidic solution, where an amount of the dissociation solution is smaller than an amount of the specimen capable of containing an antigen, to dissociate the sedimented particle composite bodies into the antigen and the particles.

In the dissociation step, the above-described particle composite bodies are dissociated (separated) into the antigen and the particles by the dissociation solution. As a result, a dissociation solution containing the antigen is obtained. Here, since the amount of the dissociation solution is smaller than the amount of "the specimen capable of containing an antigen" which is used in the above-described mixing step, the concentration of the antigen in the dissociation solution is higher than the concentration of the antigen in "the specimen capable of containing an antigen" which is used in the above-described mixing step. That is, a solution (an antigen-concentrated solution) in which the concentration of the antigen has been concentrated is obtained by the dissociation step.

[Dissociation Solution]

The dissociation solution is not particularly limited as long as it is an alkaline or acidic solution.

The alkaline solution is not particularly limited; however, specific examples thereof include an aqueous NaOH solution and an aqueous KOH solution. Among them, an aqueous NaOH solution is preferable due to the reason that the effects and the like of the present invention are more excellent.

The acidic solution is not particularly limited; however, specific examples thereof include an aqueous HCl solution, an aqueous $H_2SO_4$ solution, and an aqueous $HNO_3$ solution. Among them, an aqueous HCl solution is preferable due to the reason that the effects and the like of the present invention are more excellent.

The dissociation solution is preferably an alkaline solution due to the reason that the effects and the like of the present invention are more excellent.

The dissociation solution preferably contains NaOH or HCl, more preferably contains NaOH, and still more preferably an aqueous NaOH solution, due to the reason that the effects and the like of the present invention are more excellent.

<Amount>

As described above, the amount of the dissociation solution is smaller than the amount of "the specimen capable of containing an antigen" which is used in the above-described mixing step.

The ratio of the dissociation solution to "the specimen capable of containing an antigen" which is used in the above-described mixing step is preferably 1/2 or less, more preferably 1/3 or less, still more preferably 1/4 or less, and particularly preferably 1/5 or less in terms of mass ratio, due to the reason that the effects and the like of the present invention are more excellent.

[Recovery Step]

The recovery step is a step of sedimenting the above-described dissociated particles using a centrifuge to recover an antigen-concentrated solution. More specifically, it is a step of dissociating the particle composite bodies into the antigen and the particles in the dissociation step described above, subsequently carrying out centrifugal separation, and sedimenting the dissociated particles to recover an antigen-concentrated solution containing the antigen.

At the timing of mixing the dissociation solution in the dissociation step, which is an alkaline or acidic solution, the re-dispersed particles are dissociated by being subjected to centrifugal separation again, and the antigen-concentrated solution of the supernatant solution is separated from the particles and recovered. The conditions for centrifugal separation in this step are preferably the same as those in the sedimentation step.

[Neutralization Step]

The neutralization step is a step of neutralizing the antigen-concentrated solution recovered in the above-described recovery step by using a neutralization solution to obtain a neutralized antigen-concentrated solution.

The antigen-concentrated solution obtained in the dissociation step is usually alkaline or acidic since a dissociation solution that is an alkaline or acidic solution is used for the dissociation in the above-described dissociation step. On the other hand, in a case where an alkaline or acidic solution is used in the spreading step described later, a first binding substance or second binding substance described later may be modified, which leads to a decrease in detection sensitivity. For this reason, in the neutralization step, the neutralization solution is used to neutralize the antigen-concentrated solution.

[Neutralization Solution]

The neutralization solution is not particularly limited; however, it is possible to use, for example, a known buffer solution.

Due to the reason that the effects and the like of the present invention are more excellent, in a case where the dissociation solution that is used in the above-described dissociation step is an alkaline solution, the neutralization solution is preferable to contain HCl (particularly, 1M HCl) and at least one selected from the group consisting of tricine, Tris, 4-(2-hydroxyethyl)-1-piperazine ethanesulfonic acid (HEPES), acetamidoglycine, glycinamide, and vicine, and in a case where the dissociation solution used in the dissociation step described above is an acidic solution, the neutralization solution is preferable to contain NaOH (particularly, 1M NaOH) and at least one selected from the group consisting of tricine, Tris, HEPES, acetamidoglycine, glycinamide, and vicine.

<Amount>

The amount of the neutralization solution is smaller than the amount of "the specimen capable of containing an antigen" which is used in the above-described mixing step.

The ratio of the neutralization solution to "the specimen capable of containing an antigen" which is used in the above-described mixing step is preferably 1/10 or less and more preferably 1/100 or less in terms of mass ratio due to the reason that the effects and the like of the present invention are more excellent.

The total amount of the above-described dissociation solution and the above-described neutralization solution is preferably smaller than the amount of "the specimen capable of containing an antigen" which is used in the above-described mixing step.

The ratio of the total of the above-described dissociation solution and the above-described neutralization solution to "the specimen capable of containing an antigen" which is used in the above-described mixing step is preferably 1/2 or less, more preferably 1/3 or less, still more preferably 1/4 or less, and particularly preferably 1/5 or less, due to the reason that the effects and the like of the present invention are more excellent.

[Spreading Step]

The spreading step is a step of carrying out spreading (spreading particle composite bodies for labeling) on an insoluble carrier having a reaction site at which a second binding substance capable of binding to an antigen in the above-described-concentrated solution obtained in the above-described concentration step has been immobilized, in a state where the particle composite bodies for labeling which are composite bodies of the antigen in the neutralized antigen-concentrated solution obtained in the neutralization step described above and a modified particle for labeling which is a particle for labeling modified with a first binding substance capable of binding to the antigen are formed.

[Capturing Step]

The capturing step is a step of capturing the particle composite bodies for labeling at the reaction site of the insoluble carrier.

[Preferred Aspect of Detection Step]

In the process (the detection step) after the spreading step, the labeling particles are preferably gold particles described later, and the modified particle for labeling is preferably a modified gold particle described later, and the particle composite bodies for labeling are preferably gold particle composite bodies described later, due to the reason that the effects and the like of the present invention are more excellent.

That is, due to the reason that the effects and the like of the present invention are more excellent, the detection step preferably includes;

- a spreading step of spreading gold particle composite bodies on an insoluble carrier having a reaction site at which a second binding substance capable of binding to an antigen in the above-described-concentrated solution obtained in the above-described concentration step has been immobilized, in a state where the gold particle composite bodies which are composite bodies of the antigen in the neutralized antigen-concentrated solution obtained in the neutralization step described above and a modified gold particle which is a gold particle modified with a first binding substance capable of binding to the antigen are formed, and
- a capturing step of capturing the gold particle composite bodies at the reaction site of the insoluble carrier.

Among the above, due to the reason that the effects and the like of the present invention are more excellent, it preferably further includes a silver amplification step of silver-amplifying the gold particle composite bodies captured in the capturing step.

Hereinafter, each of the steps included in the above suitable aspect will be described.

[Spreading Step]

The spreading step is a step of carrying out spreading (spreading gold particle composite bodies) on an insoluble carrier having a reaction site at which a second binding substance capable of binding to an antigen in the above-described-concentrated solution obtained in the above-described concentration step has been immobilized, in a state where the gold particle composite bodies which are composite bodies of the antigen in the neutralized antigen-concentrated solution obtained in the neutralization step described above and a modified gold particle which is a gold particle modified with a first binding substance capable of binding to the antigen are formed.

[Gold Particle Composite Body]

As described above, in the spreading step, first, the gold particle composite bodies which are composite bodies of the antigen in the neutralized antigen-concentrated solution obtained in the neutralization step described above and a modified gold particle which is a gold particle modified with a first binding substance capable of binding to the antigen are formed.

(Modified Gold Particle)

The modified gold particle is a gold particle modified with the first binding substance capable of binding to an antigen.

(1) Gold Particle

The gold particle is not particularly limited; however, it is preferably a gold colloid particle due to the reason that the effects and the like of the present invention are more excellent.

In a case where the method according to the embodiment of the present invention includes a silver amplification step described later, the gold particle acts as a catalyst that reduces silver ions in the silver amplification step.

The particle diameter of the gold particle is preferably 5 nm to 500 nm, more preferably 7 nm to 300 nm, and still more preferably 10 nm to 200 nm, due to the reason that the effects and the like of the present invention are more excellent.

The particle diameter of the gold particle can be determined by the same method as the method for the particle in the mixing step described above.

(2) First Binding Substance

The first binding substance is not particularly limited as long as it is capable of binding to the above-described antigen; however, due to the reason that the effects and the like of the present invention are more excellent, it is preferably a protein, more preferably an antibody (for example, a polyclonal antibody or a monoclonal antibody), and from the viewpoint of achieving higher detection sensitivity, it is still more preferably a monoclonal antibody.

The above antibody is not particularly limited. However, it is possible to use, for example, an antiserum prepared from a serum of an animal immunized with an antigen, or an immunoglobulin fraction purified from an antiserum. In addition, it is possible to use a monoclonal antibody obtained by cell fusion using spleen cells of an animal immunized with an antigen, or a fragment thereof [for example, $F(ab')_2$, Fab, Fab', or Fv]. The preparation of these antibodies can be carried out by a conventional method.

In a case where the antigen is LAM, examples of the first binding substance include the A194-01 antibody described in WO2017/139153A. The entire content disclosed in WO2017/139153A relating to the A194-01 antibody is incorporated in the present specification as a part of the disclosure of the present specification.

In a case where the antigen is LAM, other examples of the first binding substance include the antibody having a sequence described as MoAb1 in paragraph No. [0080] of WO2013/129634A. The entire content disclosed in WO2013/129634A relating to the MoAb1 antibody is incorporated in the present specification as a part of the disclosure of the present specification.

(3) Method of Manufacturing Modified Gold Particle

The method of manufacturing the modified gold particle is not particularly limited, and a known method can be used.

Examples thereof include a chemical bonding method such as a method of utilizing the fact that gold and an SH group are chemically bonded and carrying out immobilization with an Au—S bond that is generated on the Au surface when an SH bond of an antibody is cleaved in a case where the SH bond thereof approaches a gold particle.

<Insoluble Carrier>

The above-described insoluble carrier is an insoluble carrier having a reaction site (a test line) at which a second binding substance capable of binding to the above-described antigen is immobilized. The insoluble carrier may have a plurality of test lines depending on the kinds of antigens (for example, a test line for influenza A type virus and a test line for influenza B type virus). In addition, the insoluble carrier may have a control line on the downstream side of the test line in order to check the spreading of the gold particle composite bodies. Further, in a case where the method according to the embodiment of the present invention includes a silver amplification step described later and, in a case where a reducing agent solution is used in the silver amplification step described later, a coloring reagent immobilization line may be provided on the downstream side of the test line in order to detect the reducing agent solution.

Examples of the specific aspect of the insoluble carrier include a nitrocellulose membrane 100 as illustrated in FIG. 1, which has from the upstream side; a gold colloid holding pad 1, a test line 2, a control line 3, and a coloring reagent immobilization line 4. Here, the gold colloid holding pad 1 is a pad that holds gold particles (modified gold particles) modified with the first binding substance, the test line 2 is a line on which the second binding substance is immobilized, the control line 3 is a line for checking the spreading, and the coloring reagent immobilization line 4 is a line for detecting the reducing agent solution described later. Here, the upstream side and the downstream side mean descriptions intended to indicate the spreading from the upstream side to the downstream side at the time when gold particle composite bodies are spread.

The more specific aspect of the insoluble carrier (or an immunochromatographic kit having the insoluble carrier) include, for example, the insoluble carrier or the immunochromatographic kit disclosed in JP5728453B, and the entire content of JP5728453B relating to the insoluble carrier and the immunochromatographic kit is incorporated in the present specification as a part of the disclosure of the present specification.

(Insoluble Carrier)

The insoluble carrier is preferably a porous carrier. In particular, it is preferably a nitrocellulose film (a nitrocellulose membrane), a cellulose membrane, an acetyl cellulose membrane, a polysulfone membrane, a polyether sulfone membrane, a nylon membrane, a glass fiber, a non-woven fabric, a cloth, a thread, or the like, and more preferably a nitrocellulose film, due to the reason that the effects and the like of the present invention are more excellent.

(Second Binding Substance)

The second binding substance is not particularly limited as long as it is capable of binding to the above-described antigen.

Specific examples and the suitable aspect of the second binding substance are respectively the same as those of the above-described first binding substance.

The second binding substance may be the same as or different from the above-described first binding substance; however, an aspect in which the second binding substance is a different substance is preferable due to the reason that the effects and the like of the present invention are more excellent.

In addition, in a case where the first binding substance and the second binding substance are antibodies, an aspect in which the antibody which is the first binding substance and the antibody which is the second binding substance are different from each other is preferable due to the reason that the effects and the like of the present invention are more excellent.

Further, in a case where the first binding substance and the second binding substance are antibodies, an aspect in which an epitope (a part of the antigen recognized by the first binding substance) of the first binding substance and an epitope (a part of the antigen recognized by the second binding substance) of the second binding substance are different from each other is preferable due to the reason that the effects and the like of the present invention are more excellent. The difference in epitope between antibodies can be confirmed by, for example, an enzyme-linked immunosorbent assay (ELISA).

<Spreading>

The method of spreading gold particle composite bodies on an insoluble carrier having a test line in a state where the gold particle composite bodies are formed is not particularly limited; however, examples thereof include a method in which the above nitrocellulose membrane 100 (or an immunochromatographic kit having the nitrocellulose membrane 100) as illustrated in FIG. 1 is prepared, and the neutralized antigen-concentrated solution obtained in the above-described neutralization step is dropwise added onto a gold colloid holding pad and moved from the upstream side to the downstream side by using the capillary action as illustrated in FIG. 1.

[Capturing Step]

The capturing step is a step of capturing the gold particle composite bodies at the reaction site of the insoluble carrier.

As described above, since the second binding substance capable of binding to an antigen is immobilized at the reaction site of the insoluble carrier, the gold particle composite bodies (the composite bodies of an antigen and a modified gold particle) which have spread on the insoluble carrier in the spreading step is captured at the reaction site (the test line) of the insoluble carrier.

The captured gold particle composite bodies are visible since it is colored by the surface plasmon or the like of a gold particle. In addition, it is also possible to estimate the concentration of the captured composite bodies using an image analysis device or the like. In this way, the antigen in the specimen can be detected.

In a case where a specimen does not contain an antigen, the gold particle composite bodies are not formed, and thus it is not captured at the reaction site of the insoluble carrier and coloration does not occur.

[Silver Amplification Step]

The silver amplification step is a step of silver-amplifying the gold particle composite bodies captured in the capturing step.

The silver amplification step is a step of forming large silver particles in the gold particle composite bodies captured at the reaction site of the insoluble carrier by providing silver ions to the insoluble carrier after the capturing step. More specifically, it is a step in which silver ions are reduced using gold particles of the gold particle composite bodies as a catalyst to form silver particles (for example, a diameter of 10 μm or more).

This significantly improves the detection sensitivity of the captured gold particle composite bodies.

<Suitable Aspect>

The method of providing silver ions to the insoluble carrier after the capturing step is not particularly limited; however, it is preferably a method in which the following reducing agent solution and the following silver amplification solution are used, due to the reason that the effects and the like of the present invention are more excellent.

Further, in addition to the reducing agent solution and the silver amplification solution, a washing solution may be used to wash the gold particle composite bodies remaining on the insoluble carrier except for the specific binding reaction. The reducing agent solution may also serve as a washing solution.

(Reducing Agent Solution)

The reducing agent solution contains a reducing agent capable of reducing silver ions. As the reducing agent capable of reducing silver ions, any inorganic or organic material or a mixture thereof can be used as long as it can reduce silver ions to silver. Preferred examples of the inorganic reducing agent include a reducing metal salt and a reducing metal composite body salt, of which the atomic valence is capable of being changed with a metal ion such as $Fe^{2+}$, $V^{2+}$, or $Ti^{2+}$. In a case where an inorganic reducing agent is used, it is necessary to remove or detoxify oxidized ions by chelating or reducing the oxidized ions. For example, in a system in which $Fe^{2+}$ is used as the reducing agent, a complex of $Fe^{2+}$, which is an oxide, is formed using citric acid or ethylenediaminetetraacetic acid (EDTA), and therefore detoxification is possible. In the present invention, it is preferable to use such an inorganic reducing agent.

As a more preferred aspect of the present invention, it is preferable to use a metal salt of $Fe^{2+}$ as the reducing agent.

It is also possible to use, as the reducing agent, a main developing agent (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), or leuco dyes) that is used in a wet-type light-sensitive silver halide photographic material, and other materials obvious to those who are skilled in the technology in the present field, such as a material disclosed in U.S. Pat. No. 6,020,117A.

As the reducing agent, an ascorbic acid reducing agent is also preferable. The useful ascorbic acid reducing agent includes ascorbic acid, an analogous substance thereof, an isomer thereof, and a derivative thereof. Preferred examples thereof include D- or L-ascorbic acid and a sugar derivative thereof (for example, γ-lactoascorbic acid, glucoascorbic acid, fucoascorbic acid, glucoheptoascorbic acid, or maltoascorbic acid), a sodium salt of ascorbic acid, a potassium salt of ascorbic acid, isoascorbic acid (or L-erythroascorbic acid), a salt thereof (for example, an alkali metal salt, an ammonium salt, or a salt known in the related technical field), ascorbic acid of the enediol type, ascorbic acid of the enaminol type, ascorbic acid of the thioenol type. Particularly preferred examples thereof include D-, L-, or D,L-ascorbic acid (and an alkali metal salt thereof) or isoascorbic acid (or an alkali metal salt thereof), and a sodium salt is a preferred salt. A mixture of these reducing agents can be used as necessary.

Due to the reason that the effects and the like of the present invention are more excellent, the reducing agent solution is preferably allowed to flow so that the angle between the spreading direction in the spreading step and the spreading direction of the reducing agent solution is 0 degrees to 150 degrees, and more preferably allowed to flow so that the angle between the spreading direction in the spreading step and the spreading direction of the reducing agent solution is 0 degrees to 135 degrees.

Examples of the method of regulating the angle between the spreading direction in the spreading step and the spreading direction of the reducing agent solution include the method described in Examples of JP2009-150869A.

(Silver Amplification Solution)

The silver amplification solution is a solution containing a compound containing silver ions. As the compound containing silver ions, it is possible to use, for example, an organic silver salt, an inorganic silver salt, or a silver complex. Preferred examples thereof include silver ion-containing compounds having a high solubility in a solvent such as water, such as silver nitrate, silver acetate, silver lactate, silver butyrate, and silver thiosulfate. Silver nitrate is particularly preferable. The silver complex is preferably a silver complex in which silver is coordinated with a ligand having a water-soluble group such as a hydroxyl group or a sulfone group, and examples thereof include silver hydroxythioether.

The organic silver salt, the inorganic silver salt, or the silver complex is contained as the silver in the silver amplification solution at a concentration of 0.001 mol/L to 5 mol/L, preferably 0.005 mol/L to 3 mol/L, and more preferably 0.01 mol/L to 1 mol/L.

Examples of the auxiliary agent of the silver amplification solution include a buffer, a preservative such as an antioxidant or an organic stabilizer, and a rate regulating agent. As the buffer, it is possible to use, for example, a buffer formed of acetic acid, citric acid, sodium hydroxide, or one of salts of these compounds, or formed of tris(hydroxymethyl)aminomethane, or other buffers that are used in general chemical experiments. These buffers are appropriately used to adjust the pH of the amplification solution to an optimum pH thereof. In addition, as the antifogging agent, an alkyl amine can be used as an auxiliary agent, and a dodecyl amine is particularly preferable. In addition, a surfactant can be used for the intended purpose of improving the solubility of this auxiliary agent, and $C_9H_{19}—C_6H_4—O—(CH_2CH_2O)_{50}H$ is particularly preferable.

Due to the reason that the effects and the like of the present invention are more excellent, the silver amplification solution is preferably allowed to flow from the direction opposite to the spreading direction in the spreading step described above and more preferably allowed to flow so that the angle between the spreading direction in the spreading step and the spreading direction of the silver amplification solution is 45 degrees to 180 degrees.

Examples of the method of regulating the angle between the spreading direction in the spreading step and the spreading direction of the silver amplification solution include the method described in Examples of JP2009-150869A.

EXAMPLES

Hereinafter, the present invention will be described in more detail with reference to Examples; however, the present invention is not limited thereto.

[1] Example A

[Preparation of Sample Solution]

Lipoarabinomannan (LAM) (02249-61, Nacalai Tesque, Inc.) (an antigen) extracted from the tubercle bacillus was added to a urine sample obtained by pooling urine samples (BioIVT LLC) of healthy subjects to prepare a sample solution (a specimen capable of containing an antigen) of a LAM concentration shown in Table 1.

Example 1

Immunochromatography of Example 1 was carried out as follows.

[Mixing Step]

Gold colloid particles (manufactured by BBI Solutions, particle diameter: 50 nm) were reacted with an anti-LAM monoclonal antibody (a substance having a specific affinity to an antigen) (WO2017/139153A (DETAILED DESCRIPTION D. Anti-LAM and Anti-PIM6/LAM Antibodies 1)) to obtain modified gold colloid particles (modified particles), which are gold colloid particles modified with an anti-LAM monoclonal antibody.

An amount of the modified particles was added to the above-described sample solution (6 mL), where the amount thereof was sufficient for an immune reaction, and the reaction was carried out for 40 minutes. In this way, a mixture containing particle composite bodies, which are composite bodies of the LAM and the modified particle, was obtained.

[Sedimentation Step]

Next, using a centrifuge, the particle composite bodies in the mixture were sedimented under the centrifugal separation conditions of centrifugal force: 8,000 G and time: 15 minutes.

[Dissociation Step]

After the sedimentation, the supernatant solution was discarded, and 0.2 mL of an aqueous solution (an alkaline solution) of 50 mmol/L NaOH was added to the particle composite bodies. After the addition, sonication treatment was carried out for 5 minutes followed by being allowed to stand for 60 minutes. In this way, the particle composite bodies were dissociated into the antigen and the particles.

The ratio of the dissociation solution to the sample solution was 1/30 in terms of mass ratio.

[Recovery Step]

Then, using a centrifuge, the dissociated particles were sedimented under the above-described centrifugal separation conditions to recover the supernatant solution (the LAM-concentrated solution) (the antigen-concentrated solution).

[Neutralization Step]

The above LAM-concentrated solution was neutralized using 0.01 mL of Tris HCl having a concentration of 1 mol/L as the neutralization solution to obtain a neutralized LAM-concentrated solution (a neutralized antigen-concentrated solution). As a result of subjecting the obtained LAM-concentrated solution to mass spectrometry, it was confirmed that the LAM concentration was concentrated by 10 times.

[Spreading Step and Capturing Step]

The obtained neutralized LAM-concentrated solution was applied to a LAM detection kit (a Clearview TB ELISA kit) manufactured by Alere Inc. to carry out the above-described spreading step and capturing step.

[Evaluation]

The coloration of the test line was visually checked and evaluated according to the following criteria.

++: It was detected clearly.

+: It was detected faintly.

−: An increase in concentration was detected.

The results are shown in Table 1. It means that the lower the lowest LAM concentration (the minimum detection sensitivity) among the LAM concentrations of the sample solution evaluated as ++ or +, the higher the detection sensitivity.

Example 2

Immunochromatography was carried out and evaluated according to the same procedure as in Example 1, except that in the mixing step, the following modified particle was used. The results are shown in Table 1.

[Modified Particle Used in Mixing Step of Example 2]

Polystyrene particles having a —COOH terminal (manufactured by Corefront, particle diameter: 2 μm) were reacted with an anti-lipoarabinomannan (LAM) monoclonal antibody (a substance having a specific affinity to an antigen) (manufactured by Nacalai Tesque, Inc., product code: 05494-84) to obtain modified polystyrene particles (modified particles) which are polystyrene particles modified with an anti-LAM monoclonal antibody. It is noted that at the time of modification, 1-ethyl-3-(3-dimethylaminopropyl) carbodiimide hydrochloride (EDC, manufactured by Nacalai Tesque, Inc.) was used to activate the —COOH terminal of the polystyrene particles.

Example 3

Immunochromatography was carried out and evaluated according to the same procedure as in Example 2, except that in the dissociation step, 0.2 mL of an aqueous solution (an acidic solution) of 50 mmol/L HCl was used instead of 0.2 mL of the aqueous solution of 50 mmol/L NaOH, and in the neutralization step, 0.01 mL of 1 mol/L Tris NaOH was used instead of 0.01 mL of 1 mol/L Tris HCl. The results are shown in Table 1.

Comparative Example 1

Immunochromatography was carried out and evaluated according to the same procedure as in Example 1 described above, except that without carrying out the concentration step (from the mixing step to the neutralization step), the above-described sample solution itself was used instead of the neutralized LAM-concentrated solution in the process after the spreading step. The results are shown in Table 1.

Comparative Example 2

Immunochromatography was carried out and evaluated according to the same procedure as in Example 1, except that in the spreading step, the following LAM-concentrated solution was used instead of the neutralized LAM-concentrated solution. The results are shown in Table 1.

[LAM-Concentrated Solution Used in Comparative Example 2]

6 mL of the above-described sample solution was concentrated by freeze-drying. Specifically, 6 mL of the above-described sample solution was frozen at −80° C. for 10 hours and then freeze-dried for 24 hours using a small freeze-dryer FDS-1000 (manufactured by TOKYO RIKAKIKAI Co., LTD.). After freeze-drying, 0.2 mL of urine containing no LAM was added to obtain a LAM-concentrated solution in which the LAM concentration was concentrated by 10 times. It is noted that as a result of composition analysis, it was confirmed that impurities such as urea and sodium phosphate were contained.

colloid holding pad 1, the test line 2, the control line 3, and the coloring reagent immobilization line 4. The gold colloid holding pad 1 is a pad that holds modified gold colloid particles which are gold colloid particles (modified particles for labeling) modified with an anti-LAM monoclonal antibody, the test line 2 is a line on which the anti-LAM monoclonal antibody is immobilized, the control line 3 is a line for checking the spreading, and the coloring reagent immobilization line 4 is a line for detecting the reducing agent solution in the silver amplification step described later.

The neutralized LAM-concentrated solution was drop-wise added onto the gold colloid holding pad. As a result, particle composite bodies for labeling, which are composite bodies of the LAM in the solution and the modified gold colloid particle (the modified particle for labeling) which is

TABLE 1

| | | Example 1 | Example 2 | Example 3 | Comparative Example 1 | Comparative Example 2 |
|---|---|---|---|---|---|---|
| Concentration step | | Present | Present | Present | Absent | Freeze-drying |
| Particle | | Gold colloid particle | Polystyrene particle | Polystyrene particle | − | − |
| Dissociation solution | | Alkaline | Alkaline | Acidic | − | − |
| LAM concentration | 0.6 ng/mL | ++ | ++ | ++ | ++ | + |
| | 0.4 ng/mL | ++ | ++ | ++ | ++ | − |
| | 0.2 ng/mL | ++ | ++ | ++ | + | − |
| | 0.1 ng/mL | ++ | ++ | ++ | − | − |
| | 0.05 ng/mL | ++ | ++ | ++ | − | − |
| | 0.03 ng/mL | ++ | ++ | ++ | − | − |
| | 0.025 ng/mL | ++ | ++ | + | − | − |
| | 0.02 ng/mL | + | + | − | − | − |
| | 0.01 ng/mL | − | − | − | − | − |
| | 0.005 ng/mL | − | − | − | − | − |

As can be seen from Table 1, Examples 1 to 3 in which the above-described concentration step was carried out exhibited high detection sensitivity as compared with Comparative Example 1 in which the above-described concentration step was not carried out and Comparative Example 2 in which concentration was carried out by freeze-drying. Among them, Examples 1 and 2 in which the dissociation solution contained NaOH exhibited higher detection sensitivity.

[2] Example B

[Preparation of Sample Solution]

Lipoarabinomannan (LAM) (02249-61, Nacalai Tesque, Inc.) (an antigen) extracted from the tubercle bacillus was added to a urine sample obtained by pooling urine samples (BioIVT LLC) of healthy subjects to prepare a sample solution (a specimen capable of containing an antigen) of a LAM concentration shown in Table 2.

Example 4

The concentration step (from the mixing step to the neutralization step) was carried out according to the same procedure as in Example 2 described above, except that the sample solution (6 mL) having the LAM concentration shown in Table 2 was used. Then, using the obtained neutralized LAM-concentrated solution (the neutralized antigen-concentrated solution), the following process after the spreading step was carried out.

[Spreading Step]

The nitrocellulose membrane 100 as illustrated in FIG. 1 was prepared, which has from the upstream side; the gold a gold colloid particle modified with the anti-LAM monoclonal antibody, were formed. In this state, the gold particle composite bodies were spread from the upstream side toward the downstream side of the nitrocellulose membrane.

[Capturing Step]

The particle composite bodies for labeling which have spread in the spreading step are captured on the test line.

[Silver Amplification Step]

The silver amplification step was carried out as follows.

<Preparation of Reducing Agent Solution>

23.6 mL of an aqueous solution of 1 mol/L iron nitrate, which was produced by dissolving iron (III) nitrate nonahydrate (manufactured by FUJIFILM Wako Pure Chemical Corporation) in water, and 13.1 g of citric acid (manufactured by FUJIFILM Wako Pure Chemical Corporation) were dissolved in 290 g of water. After all of the substances were dissolved, 36 mL of nitric acid (10% by mass) was added thereto while stirring with a stirrer, 60.8 g of ammonium iron (II) sulfate hexahydrate (manufactured by FUJIFILM Wako Pure Chemical Corporation) was added thereto, and the resultant solution was used as the reducing agent solution.

<Preparation of Silver Amplification Solution>

8 mL of a silver nitrate solution (including 10 g of silver nitrate) and 24 mL of an aqueous solution of 1 mol/L iron nitrate were added to 66 g of water. Further, this solution was mixed with a solution obtained by dissolving in advance 5.9 mL of nitric acid (10% by mass), 0.1 g of dodecyl amine (manufactured by FUJIFILM Wako Pure Chemical Corporation), and 0.1 g of a surfactant $C_{12}H_{25}$—$C_6H_4$—O—$(CH_2CH_2O)_{50}H$ in 47.6 g of water, and the resultant solution was used as the silver amplification solution.

<Spreading of Reducing Agent Solution>

In the nitrocellulose membrane, the reducing agent solution prepared as described above was allowed to flow from the same direction as that of the spreading step described above (from the upstream side).

<Spreading of Silver Amplification Solution>

After the coloring reagent immobilization line was discolored, the silver amplification solution prepared as described above was allowed to flow from the direction opposite to the spreading direction (from the downstream side) in the spreading step. In this way, the particle composite bodies for labeling captured on the test line were silver-amplified.

[Evaluation]

The coloration of the test line was visually checked and evaluated according to the following criteria.

++: It was detected clearly.

+: It was detected faintly.

−: An increase in concentration was detected.

The results are shown in Table 2. It means that the lower the lowest LAM concentration (the minimum detection sensitivity) among the LAM concentrations of the sample solution evaluated as ++ or +, the higher the detection sensitivity.

Comparative Example 3

Immunochromatography was carried out and evaluated according to the same procedure as in Example 4 described above, except that without carrying out the concentration step (from the mixing step to the neutralization step), the above-described sample solution itself was used instead of the neutralized LAM-concentrated solution in the process after the spreading step. The results are shown in Table 2.

TABLE 2

| | | Example 4 | Comparative Example 3 |
|---|---|---|---|
| Concentration step | | Present | Absent |
| Particle | | Polystyrene particle | − |
| Dissociation solution | | Alkaline | − |
| LAM concentration | 0.2 ng/mL | ++ | ++ |
| | 0.1 ng/mL | ++ | ++ |
| | 0.05 ng/mL | ++ | + |
| | 0.03 ng/mL | ++ | − |
| | 0.01 ng/mL | ++ | − |
| | 0.005 ng/mL | + | − |
| | 0.003 ng/mL | − | − |
| | 0.001 ng/mL | − | − |

As can be seen from Table 2, Example 4 in which the above-described concentration step was carried out exhibited high detection sensitivity even in the immunochromatography in which silver amplification was carried out, as compared with Comparative Example 3 in which the above-described concentration step was not carried out.

EXPLANATION OF REFERENCES

1: gold colloid holding pad

2: test line

3: control line

4: coloring reagent immobilization line

100: nitrocellulose membrane

What is claimed is:

1. Immunochromatography method comprising:

mixing a specimen that may contain an antigen and a modified particle, which is a particle modified with a substance having a specific affinity to the antigen, to obtain a mixture containing particle composite bodies which are composite bodies of the antigen and the modified particle, wherein the substance having a specific affinity to the antigen is a monoclonal antibody;

sedimenting the particle composite bodies in the mixture using a centrifuge;

dissociating the particle composite bodies into the modified particle and the antigen by mixing the sedimented particle composite bodies with a dissociation solution that is an alkaline solution, where an amount of the dissociation solution is smaller than an amount of the specimen capable of containing an antigen;

recovering an antigen-concentrated solution by sedimenting the dissociated modified particle using a centrifuge and then recovering the supernatant solution which is the antigen-concentrated solution;

neutralizing the antigen-concentrated solution using a neutralization solution to obtain a neutralized antigen-concentrated solution;

adding dropwise the neutralized antigen-concentrated solution onto a gold colloid holding pad, which is a pad that comprises modified gold particles for labeling which are gold particles for labeling modified with a first binding substance capable of binding to the antigen, of an insoluble carrier having the gold colloid holding pad at an upstream site and a reaction site at which a second binding substance capable of binding to the antigen has been immobilized at a downstream site, the second binding substance is different from the first binding substance;

spreading gold particle composite bodies for labeling on the insoluble carrier by using a capillary action, in a state where the gold particle composite bodies for labeling which are composite bodies of the antigen in the neutralized antigen-concentrated solution and the modified gold particles for labeling are formed; and capturing the gold particle composite bodies for labeling at the reaction site of the insoluble carrier, wherein the specimen capable of containing an antigen is urine, wherein the antigen is lipoarabinomannan.

2. The immunochromatography method according to claim 1, wherein the immunochromatography further comprising silver-amplifying the captured gold particle composite bodies for labeling.

3. The immunochromatography method according to claim 1, wherein the modified particle that is used in the mixing has a particle diameter of 50 nm to 3,000 nm.

4. The immunochromatography method according to claim 1, wherein a ratio of the dissociation solution to the specimen capable of containing an antigen is 1/5 or less in terms of mass ratio.

5. The immunochromatography method according to claim 1, wherein the dissociation solution contains NaOH.

6. The immunochromatography method according to claim 1, wherein the neutralization solution contains HCl and at least one selected from the group consisting of tricine, Tris, HEPES, acetamidoglycine, glycinamide, and vicine.

* * * * *